United States Patent [19]
Wolfinbarger et al.

[11] Patent Number: 5,275,954
[45] Date of Patent: Jan. 4, 1994

[54] PROCESS FOR DEMINERALIZATION OF BONE USING COLUMN EXTRACTION

[75] Inventors: Lloyd Wolfinbarger, Norfolk; Scott Bottenfield, Virginia Beach, both of Va.

[73] Assignee: Lifenet, Virginia Beach, Va.

[21] Appl. No.: 664,675

[22] Filed: Mar. 5, 1991

[51] Int. Cl.$^5$ .............. B01D 11/02; G01N 1/18; G01N 27/00; C07K 3/02

[52] U.S. Cl. .............. 436/74; 422/69; 422/70; 422/261; 424/549; 424/572; 436/79; 436/150; 436/163; 436/164; 436/177; 436/178; 530/422; 530/423; 530/424; 530/426

[58] Field of Search .............. 436/74, 79, 149, 150, 436/163, 164, 177, 178; 422/69, 70, 101, 261; 424/549, 572; 530/422-

[56] References Cited

U.S. PATENT DOCUMENTS

| | | | |
|---|---|---|---|
| 240,855 | 5/1881 | Seltsam et al. | 422/261 X |
| 2,074,988 | 3/1937 | O'Brien et al. | 530/422 X |
| 2,517,487 | 8/1950 | Hill et al. | 422/261 X |
| 2,968,593 | 1/1961 | Rapkin | 424/549 |
| 3,539,549 | 11/1970 | Greenfield | 530/424 X |
| 3,615,235 | 10/1971 | Hrdina | 422/70 |
| 3,814,584 | 6/1974 | Tocci | 436/178 |
| 4,042,671 | 8/1977 | Bowdish | 422/261 X |
| 4,172,128 | 10/1979 | Thiele et al. | 424/549 |
| 4,199,496 | 4/1980 | Peniston et al. | 530/422 X |
| 4,221,568 | 9/1980 | Boettger | 422/64 X |
| 4,280,905 | 7/1981 | Gunkel et al. | 210/198.2 |
| 4,294,753 | 10/1981 | Urist | 530/422 X |
| 4,394,370 | 7/1983 | Jefferies | 424/549 |
| 4,396,560 | 8/1983 | Stofer | 422/261 |
| 4,427,583 | 1/1984 | England et al. | 426/657 X |
| 4,434,094 | 2/1984 | Seyedin et al. | 424/549 X |
| 4,440,750 | 4/1984 | Glowacki et al. | 424/549 |
| 4,533,643 | 8/1985 | Bell et al. | 436/178 |
| 4,554,132 | 11/1985 | Collins | 436/178 X |
| 4,603,115 | 7/1986 | Schweighardt | 436/178 |
| 4,634,680 | 1/1987 | Kingsley | 436/178 |
| 4,666,858 | 5/1987 | Magnuson et al. | 436/178 X |
| 4,724,216 | 2/1988 | Young et al. | 436/74 X |
| 4,735,782 | 4/1988 | Wicker et al. | 436/178 X |
| 4,824,939 | 4/1989 | Simpson | 530/426 X |
| 4,871,675 | 10/1989 | Coupek et al. | 422/101 X |

FOREIGN PATENT DOCUMENTS 9003209  4/1990  PCT Int'l Appl. .............. 436/178

OTHER PUBLICATIONS

K. L. Nelson et al. "Correlated Organic Laboratory Experiences" 1975, Brigham Young University Press; Provo, Utah, p. 100.
Process Validation for Demineralization of Ground Human Bone Matrix; Jae Eun Lee & Lloyd Wolfinberger; Oct. 1990.
Validation of Processing Steps in Bone Demineralization; J. E. Lee, L. Wolfinbarger, Jr., S. Bottenfield, M. Conley, & M. John; Sep. 1990.

*Primary Examiner*—Jill A. Johnston
*Assistant Examiner*—Arlen Soderquist
*Attorney, Agent, or Firm*—Sandler Greenblum & Bernstein

[57] ABSTRACT

A process and apparatus are disclosed for the demineralization of ground bone particles or pieces of cancellous or cortical bone. The apparatus includes multiple solution reservoirs which supply solutions to be pumped into one or more columns filled with bone samples to be demineralized. Solvent outflowing from the column(s) can be monitored for pH, calcium ion concentration or conductivity as a basis for determining when demineralization is complete. During the delipidization phase of processing, lipid solute can be monitored by photometry, or a small assay of the eluent can be dropped into deionized water to see whether a precipitate develops. Flow through the apparatus, including the types and amounts of solutions to be flowed through the apparatus, can be manually or computer controlled.

28 Claims, 7 Drawing Sheets

Fig_ 4

Fig_ 5

Fig_ 9

Fig_ 10

PROCESS FOR DEMINERALIZATION OF BONE USING COLUMN EXTRACTION

BACKGROUND OF THE INVENTION

1. Field of the Invention

The invention concerns an apparatus which is suitable for permeating solid materials with various solutions and is particularly directed to processes for the demineralization of bone tissue. The invention is also directed to an apparatus for performing the processes.

2. Description of Background Information

It is known that implementation of acid demineralized bone (DB) in the form of a powder in extraskeletal sites stimulates new bone formation. Various research groups (Syftestad, 1982; Urist et al., 1967; Urist and Strates, 1970; Urist & Strates, 1971; Urist et al., 1983) have suggested that a noncollagenous protein present in demineralized bone has the ability to induce new bone formation when present within the implanted bone matrix.

Procedures presently utilized to demineralize ground bone fragments involve the use of ethanol to remove lipids and hydrochloric acid to remove the mineral component of bone.

It is also known to treat bones and bone particles to render them biocompatible so that they can be implanted in living animal and human bodies without being rejected. Included among the known methods for treating bone is the delipidization of bone using ethanol or chloroform. It is further known to demineralize bone matrix with an inorganic acid such as hydrochloric acid.

Demineralized, defatted bone can be further treated with antibacterial and antifungal agents to help prevent infection upon implantation into a living organism.

SEYEDIN et al., U.S. Pat. No. 4,434,094, describes the fragmentation of bone into small pieces and subsequent treatment by extraction with ethanol ethylacetate to remove lipids from the bone fragments. Calcium phosphate is next dissolved from the bone matrix by contacting the bone particles with dilute hydrochloric acid for one hour up to several days.

JEFFERIES, U.S. Pat. No. 4,394,370, discloses a similar method of demineralization wherein bones are first cleaned and extracted with absolute ethanol followed by anhydrous ethyl ether. The bones are then pulverized and sieved to a standard particle size. Demineralization is achieved through extraction with 0.5N hydrochloric acid for at least three hours followed by multiple washes in sterile distilled water to remove calcium and acid residues, followed by multiple sequential 60-minute washes in ethanol and anhydrous ether.

Although it is well known to defat and demineralize bone for implantation purposes, known methods of demineralizing and removing lipids have been extremely tedious, labor intensive and slow. Furthermore, an excessive amount of handling and/or exposure of the bone to non-sterile conditions has been necessary during the various phases of processing.

Delipidization and demineralization of bone matrix has been conducted largely through soaking the bone matrix in extraction solutions. Demineralization of bone involves the solubilization of hydroxyapatitic materials using fairly strong acids. As demineralization proceeds, the solubilized hydroxyapatitic materials act to buffer the acidic solution thereby raising the pH. This renders the acid less effective, and demineralization thus takes longer, or greater volumes of acid are required, because the acid solution must be completely changed to restore the pH to an effective level.

SUMMARY OF THE INVENTION

One advantage of the present invention is achieved by continually changing the acid solution during the extraction process using the apparatus(es) and processes described herein, so that the solubilized minerals are continually removed and thus solubilization of bone mineral continues with essentially similar effectiveness over time. Thus, bone processing is accomplished in less time using less total volumes of solutions.

Accordingly, it is one object of the present invention to provide an apparatus for the delipidization and demineralization of bones, bone pieces and bone particles that minimizes the necessity of exposing treated bone to non-sterile conditions. Included in this object is the provision of a treatment column which allows freezing and storing of the bone upon removal of the column from the apparatus, without requiring the bone to be removed from the treatment column.

It is another object of the present invention to provide an apparatus and method for the simultaneous delipidization and demineralization of multiple bone samples.

It is a further object of the present invention to provide an apparatus and process for delipidization and demineralization of bone samples which is less tedious and labor intensive than the methods known to the prior art. This object is to be achieved through automation of the processes involved, as well as by simultaneous processing of multiple samples.

Other objects and advantages of the present invention and advantageous features thereof will become apparent as the description proceeds herein.

Included in the description is an apparatus for processing solid matter comprising at least one column for containing the solid matter where each column has an upper end and lower end. Each lower end has an inlet valve attached and each upper end has an outlet valve attached. Each column is adapted to contain solid matter during the extent of processing. The apparatus further includes a driving mechanism for conducting flow of solutions through each column, which is preferably at least one peristaltic pump, for processing the solids therein; column clamps for supporting each column in a vertical position during processing; and solution reservoirs for holding the solutions which are to be conducted through the columns. Each column is adapted to be removed from its supports after processing and each inlet and outlet valve is adapted to be closed to allow for sterile storage of the solid matter located in each column.

Preferred solid materials to be processed in the apparatus include particulate bone and strips of cortical bone. The entire apparatus can be contained within a refrigeration system which is capable of maintaining the apparatus at a processing temperature range of 0° to 38° C.

The invention further includes detecting devices for detecting solutions which exit the outlet side of the column, which are referred to as eluent. The detecting device(s) may detect pH, calcium ion concentration or conductivity. Included among the detecting devices are calcium specific electrodes for detecting calcium ions Detecting devices may also include flow rate detectors which connect each solution reservoir with a solution switching mechanism and the driving mechanism. Flow rate detectors may include optical drop counter devices which connect each solution reservoir with a flow switching device which connects to the driving mechanism.

The present invention further may include a computer controller for automated control of flow through the apparatus; on the other hand, the apparatus may be manually controlled. The detecting devices may provide feedback to the computer control means to enable the computer to control flow and switching of solutions.

Flow control and switching of solutions may be pneumatically driven or electrically driven by solenoid controllers.

The outlet side of each column may include a mechanism for preventing backflow of contaminants, which is preferably an optical drop counter device.

The invention is also directed to a process for extracting undesirable constituents of a solid material, which comprises loading a solid material into at least one column, where each column has an inlet valve and an outlet valve; flowing a solution through each column; detecting a characteristic of a solute which is present in the solution as the solution exits each column; terminating flow of the solution once a desired characteristic of the solute is detected and thereafter flowing a different solution through each column.

The process further encompasses detecting a characteristic of a second solute which is present in the subsequent solution as the solution exits each column; and terminating flow of the solution once a desired characteristic of the second solute is measured.

Furthermore, the process encompasses flowing additional solution through each column and detecting a characteristic of each solute which is present in each solution as each solution exits each column.

The solutions employed in the process include lipophilic solvents, sterile deionized water, buffers and acids.

The lipophilic solvents may include ethanol, chloroform or other lipophilic solvents known in the art. The acids employed include dilute hydrochloric acid and other organic or inorganic acids known and used in the art for demineralization of bone.

Detection methods for the lipophilic solvents include detecting the absorbance of the solute dissolved in the lipophilic solution, and dripping a sample of the lipophilic solution into deionized water to determine whether a precipitate forms. Detection methods for the acidic solvents include measuring the pH of the acidic solution, detecting the presence of calcium ions in the acidic solution by measuring the calcium ion concentration of the solution, and measuring conductivity.

The flow control for the processes may be accomplished by at least one pneumatic control valve or at least one electric solenoid controlled valve.

Each flow control valve may be computer controlled or manually controlled. Any combination of or all of the detecting devices may provide feedback to a computer controller for providing information useful to the computer to control flow or to decide when to switch solutions.

The columns of the apparatus may be readily sealed and removed from the apparatus, with the processed solid material still within the columns, for sterile storage of the processed solid material.

Also included in the invention, is a fine mesh bag which may be preloaded with solid material and then loaded into the column. The fine mesh bag is preferably used for dental bone and other small solid particles in the range of 250μ to 700μ. The bag is preferably formed of polyester but may be made of other materials which are resistent to and nonreactive with the solutions that it will interface with during processing. The fine mesh bag has a porosity which is small enough to retain the smallest solid particles with which it will be loaded, yet large enough to permit the escape of gases which are formed during processing.

BRIEF DESCRIPTION OF THE DRAWINGS

The present invention is further explained in the description which follows with reference to the drawings, illustrating, by way of non-limiting examples, various embodiments of the invention, with like reference numerals representing similar parts throughout the several views, and wherein.

DESCRIPTION OF THE PREFERRED EMBODIMENTS

Figure 1:
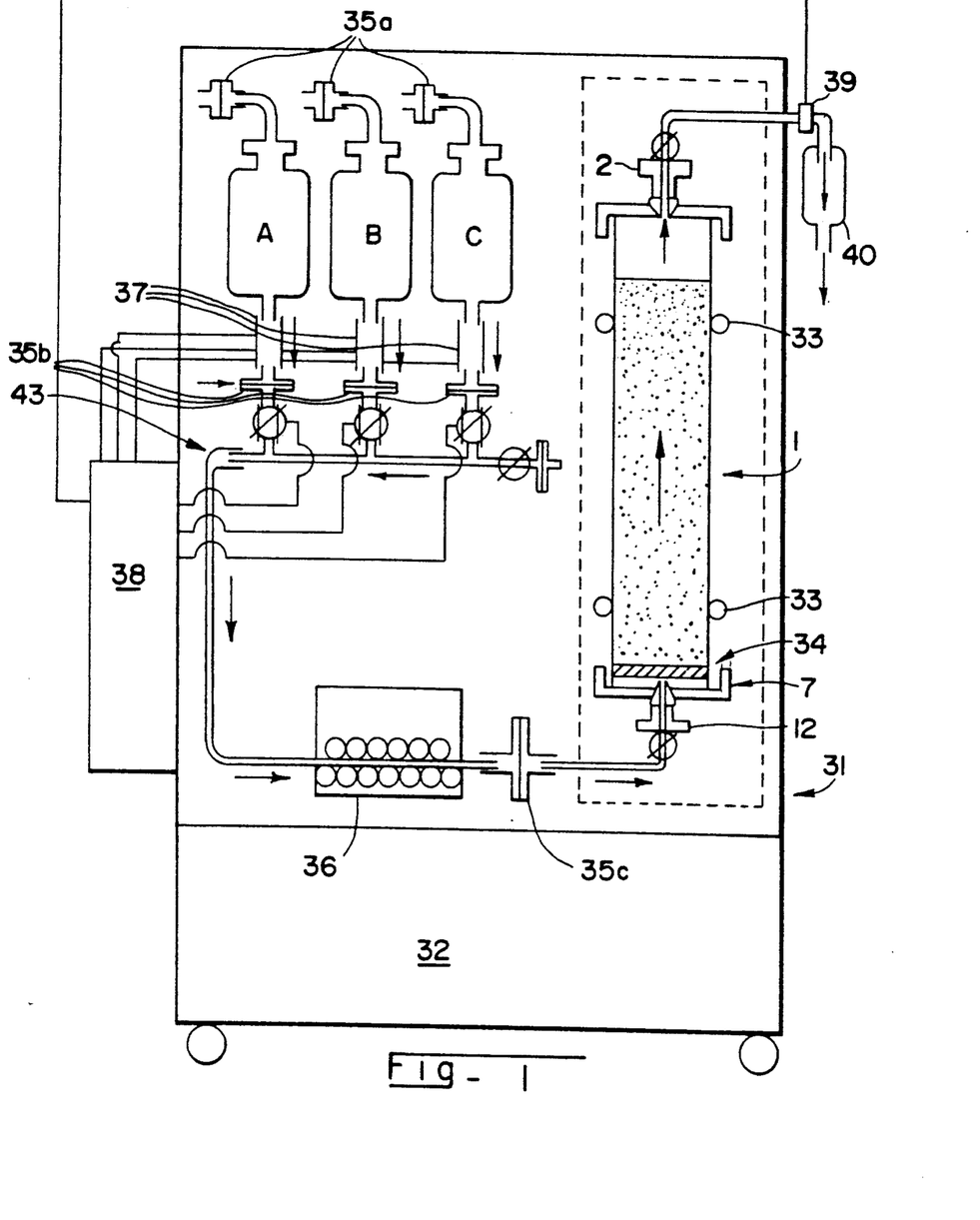
FIG. 1 is a plan view of a complete bone demineralization apparatus according to the present invention.

Referring now to the drawings in detail, FIG. 1 shows a complete apparatus for the delipidization and demineralization of bone samples. Generally cylindrical column 1 is removably secured in a vertical position by column clamp supports 33. Columns clamp supports may, for example, be formed by rubber coating spring steel of the required dimensions. Containers for holding solutions A, B and C each have sterile in-line filters 35a attached upstream of their respective inputs to prevent bacterial and other contamination of the sterile solutions contained therein. The invention is not limited to three containers (e.g., reservoirs) for holding solutions as shown by the embodiment in FIG. 1, but may use more or less than three reservoirs, depending on the number of different solutions that are to be used for the particular process in question. For example, one may wish to further treat the demineralized bone subsequent to defatting and demineralizing with antibacterial solutions, antifungal solutions, vitamins, bone morphogenetic protein or other osteogenic factors, collagens or other proteins, etc.

Furthermore, the apparatus is not limited to use only for demineralization of bone. It can be used advantageously in many other instances where it is desired to permeate a solid/particulate material with one or more solutions. It is particularly useful when it is desired to maintain the solid/particulate material under sterile conditions during processing. Other possible uses of the apparatus include, but are not limited to: crosslinking of collagen-containing implant materials; treatment of natural blood vessels to render them nonantigenic; the treatment of soft tissue implants with, for example, heparin to render them non-thrombogenic. Another set of in-line filters 35b, similar to filters 35a, is attached to the outflow side of reservoirs A, B and C, upstream of the respective outflow valve for each line.

Optionally, flow rate monitors 37, which may for example be optical drop counters, may be connected between the outflow side of reservoirs A, B and C and in-line filters 35b, for providing feedback to controller 38 for flow control. In this embodiment, a 3 to 1 manifold includes switching means for controlling whether solution A, B or C is to pass through to peristaltic pump 36.

The peristaltic pump 36 which is illustrated in FIG. 1 is not necessarily required to drive the flow through the apparatus. Other pumps and driving mechanisms known in the art can be used. Yet another in-line filter 35c is attached in line with the outflow side of pump means 36. From the outflow side of the in-line filter the tubing is next attached to inlet valve apparatus 12 which is attached to the inlet part of the column at the bottom end 7 of the column. Bed support 34 may be placed on top of bottom end 7. Optionally, a manifold (i.e. 1:3, 1:4 or some other ratio) can be connected to the outflow side of pump 36 to enable parallel processing of multiple columns, as shown schematically in FIG. 2.

The tubing that is attached to the outlet valve 2 of the column leads to a waste receptacle where the eluent is disposed of. A flow rate monitor 40 may optionally be connected in line between each column and the waste receptacle to prevent backflow of waste eluent into each column. Furthermore, a monitoring device 39 may be attached in-line to the outflow side of each column, before the waste receptacle and before, the optional flow rate monitor 40. Such monitoring device may include, e.g., photometers, pH monitors, calcium ion specific electrodes and conductivity probes. Monitoring (detecting) device 39 provides feedback to controller 38 (e.g., a CPU) to enable controller 38 to decide when to change the flow from one solution reservoir to the next.

The entire apparatus described above is preferably contained within a refrigeration cabinet 31. A conventional refrigeration system 32 is used which is capable of maintaining the apparatus in the range of 0° to 38° C. All apparatus components are adapted to be removed from the refrigeration cabinet 31. The apparatus can be controlled manually or automatically. As stated above, the flow meters and other monitoring devices 37, 39 and 40 may provide feedback to a computer 38 for automated control of solution flow.

Figure 2:
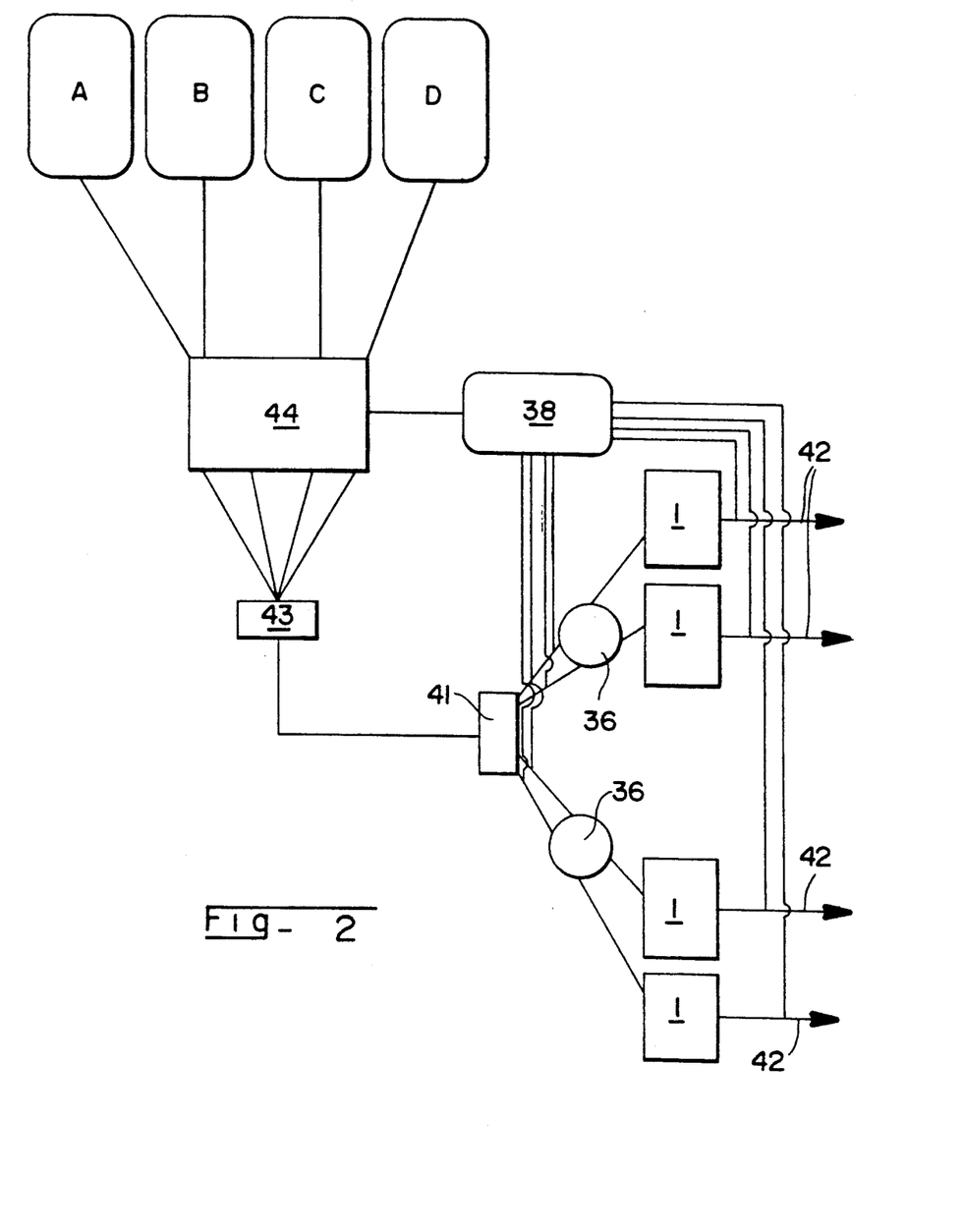
FIG. 2 is a schematic diagram of a control system for an apparatus using a plurality of demineralizing columns and solutions adapted to be conducted through the columns.

FIG. 2 is a schematic diagram of an embodiment of the present invention for processing multiple samples simultaneously in a plurality of columns. In this embodiment, four solution reservoirs (A, B, C and D) are connected to flow control mechanism 44. Flow control mechanism 44 (e.g., a plurality of flow control valves) may be either pneumatically driven or driven by electric solenoid and may be manually controlled or controlled by computer 38. If the computer option is chosen, the computer should be programmed, with the option to be reprogrammed, to control the time intervals of the control mechanism 44. The peristaltic pump(s) can be set to deliver a flow rate that is independent of the controller input. The flow is passed through e.g., a 4:1 manifold 43, and then through e.g., a 1:4 manifold 41 in this embodiment to connect to two peristaltic pumps 36. Each peristaltic pump is connected to two columns 1 so that four samples may be processed in parallel. Eluent exits the columns at 42, in the fashion described above with respect to the column of FIG. 1.

Flow control mechanism 44 shown in the schematic drawing of FIG. 2, includes flow control monitors which provide feedback to computer controller 38, so that the controller can determine whether to maintain, increase or decrease the detected flow rate(s). Feedback to unit 38 is also provided by monitoring device 39 (not numbered) at the eluent side of the columns 1, so that the controller can determine when each stage of processing is complete. The controller, upon each such determination, shuts off flow from the solution reservoir that is then supplying solution via flow control mechanism 39, and initiates flow from the next solution reservoir in the processing sequence.

Optionally, flow control valves (not shown) may also be located between 1:4 manifold 41 and peristaltic pumps 36, and these valves may be optionally controlled by computer controller 38 or manually controlled. Flow control valves, when positioned into this location, allow differential processing of parallel columns 1. For example, one column may contain smaller particles than the other three and require less demineralization time. In such a case, controller 38 would sense, through feedback from a pH or calcium ion monitor 39, that demineralization is complete in one column before it is complete in the other three columns. The controller would then close the valve near the peristaltic pump which leads to the completely demineralized sample, while hydrochloric acid would continue to be pumped through the remaining three columns. The optional flow control valves would, of course, also permit one or more columns to be completely shut down when less than four samples are to be processed.

Figure 3:
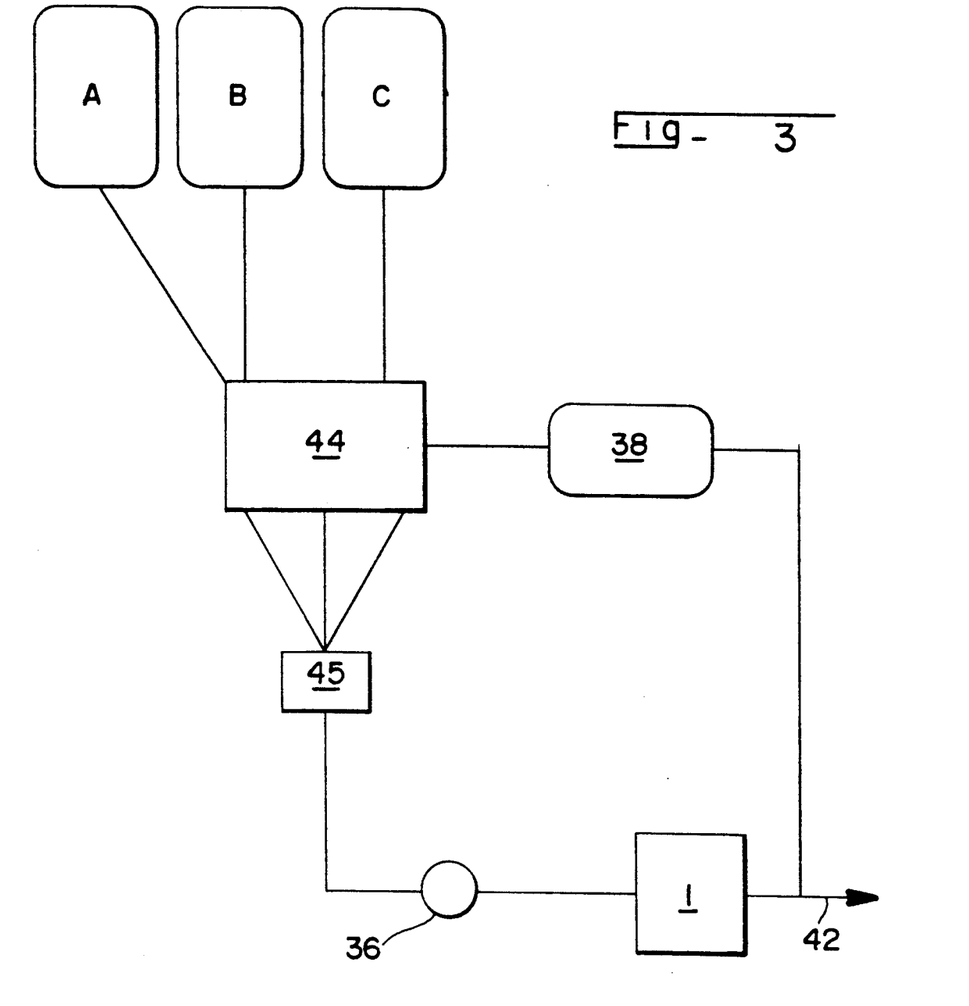
FIG. 3 is a schematic diagram of a control system for an apparatus using a single demineralizing column, as basically shown in FIG. 1, and solutions adapted to be conducted through the column.

FIG. 3 is a schematic diagram of an embodiment of the present invention for processing one sample at a time in column 1, as essentially illustrated in FIG. 1. Three solution reservoirs (A, B, and C) are shown, but more or less reservoirs may be supplied as discussed earlier. Flow control mechanism 44 is similar to that shown in FIG. 2; but in this instance, only three lines are controlled in and out of the mechanism. Flow continues to a 1:3, manifold 45 and a single peristaltic pump 36. An optional flow control valve is not necessary at this location for this embodiment, since flow is either existent or non-existent to the single column in this embodiment; and because this single column can be controlled at device 44.

Similarly to FIG. 2, computer controller 38 receives feedback from the monitor(s) at the eluent side of column 1 and from the flow rate monitor(s) at (or upstream of) the location of control mechanism 44, for control of solution source switching and flow rate, respectively. As in the embodiment of FIG. 2, controller 38 comprises, e.g., a CPU capable of controlling flow in response to the detected flow rate(s) and eluent.

Figure 4:
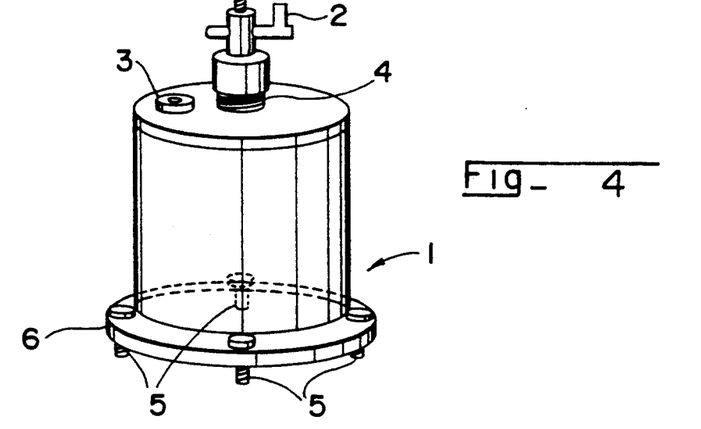
FIG. 4 is an embodiment of the top portion of a column shown in FIG. 1 which is adapted for processing, e.g., dental bone.

FIG. 4 shows a preferred embodiment of the top component of a column 1 useful in processing, e.g., "dental bone" (i.e. bone particles ranging in size from $250\mu$ to $700\mu$). This device is not limited, however, to use for the demineralization of dental bone, but also in processing finely ground bone particles, and may also be used in any production process requiring the retention of some desired size range within a permeable bag while solvent solutions are passed over and through the particles to affect a washing or extraction, or deposition of, solute onto the particles.

The top end of column 1 includes a threaded outlet port 4 to which an outlet valve 2 is connected via screw threads. The top end also contains a levelling device 3 which assists in fixing the column in a vertical position to help ensure uniform flow of solvent during processing. Levelling device 3 can, for example, be a well-known bubble type level. When the column is positioned vertically, the bubble in the level centers in the fluid contained in the level.

At the bottom end of column ?, is located a flange 6 which accommodates an "O" ring (not shown) for securing the connection to be made between the top and bottom components of the column. Protruding through flanges 6 are threaded connecting bolts 5, which are preferably formed from teflon or polypropylene.

Preferred materials for constructing the column are glass or polycarbonate, but other construction materials known in the art which are inert to the solutions to be passed through the column may also be used.

Preferred dimensions for column when used for processing dental bone, are 7.5 cm for the height of the column and 21.5 cm for the diameter of the column. These dimensions are appropriate for the quantity of bone matrix expected to be obtained from a tissue donor. To accommodate more or less quantity of bone material, the height of the column should be adjusted while leaving the diameter unchanged. The height of the column can be increased to optimally accommodate larger size particles of bone material, but this is not absolutely essential. Especially for smaller bone particles, selection of the appropriate column geometry appears to be important in permitting the escape of $CO_2$ gas formed during processing. The escape of $CO_2$ gas helps prevent the bone particles from compacting since the particles swell as demineralization proceeds, and ensure uniform flow of solutions through and over the bone particles. With larger bone particles/pieces, the dimensions of the column appear to be of minimal importance, requiring only that an attempt be made to reduce the volume of solutions inside the column not occupied by the bone.

Figures 5, 9, 10:
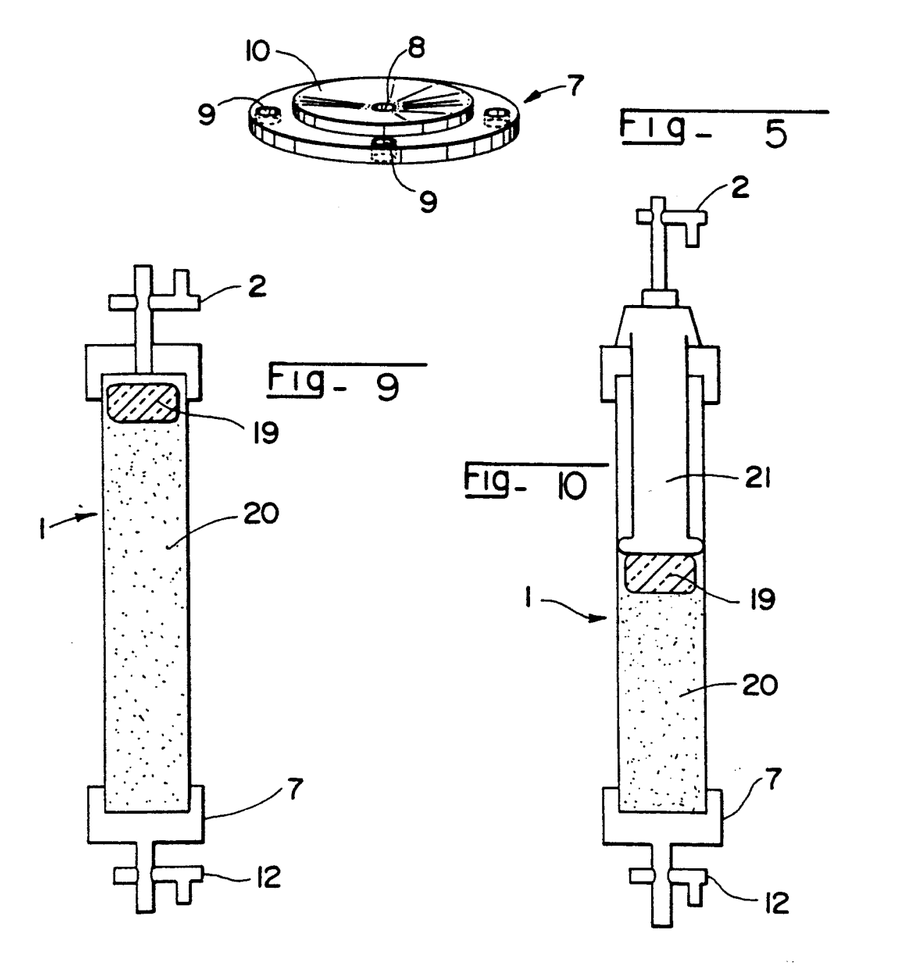
FIG. 5 is a bottom portion of a column adapted to engage the top portion shown in FIG. 4.
FIG. 9 is a view of a column similar to that of FIG. 4, with a top filter which is used to retain solid matter within the processing column.
FIG. 10 is a sectional view of another embodiment of a column similar to that of FIG. 9, and which includes a compacting plunger.

FIG. 5 shows a bottom component 7 which is designed to connect with the bottom end of column 1, via bolt holes 9. A threaded inlet port 8 located at the center of the member 7 accommodates an inlet valve mechanism and conducts inflow of solvents into the assembled column.

Figure 6:
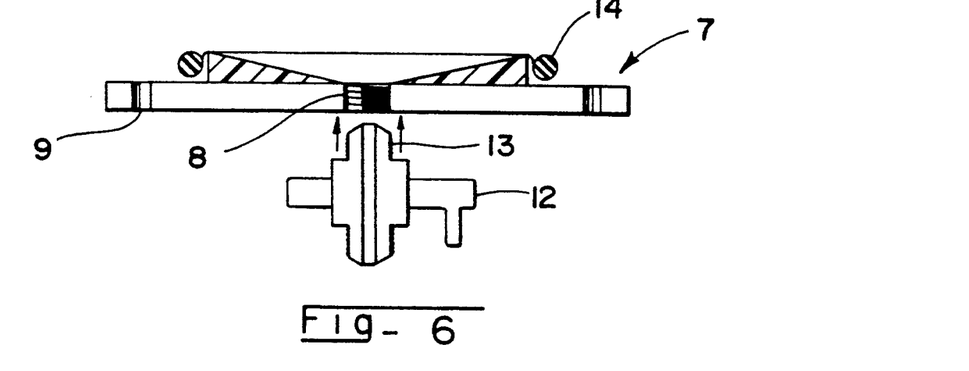
FIG. 6 shows a longitudinal sectional view of the bottom component of FIG. 5, together with an inlet valve.

FIG. 6 is a sectional view depicting the engagement of an inlet valve mechanism 12 with inlet port 8 via threads 13. A preferred valve mechanism is a $\frac{1}{4}$" or $\frac{1}{8}$" MULTIFIT ® valve, constructed of teflon, but any two-way valve mechanism which is both resistant to the solvents to be passed through it and capable of sealing inlet port 8 in a sterile fashion may be used. FIG. 6 also shows a fine mesh screen 11 which is designed to fit over the center portion 10 of annular bottom component 7, and is designed to prevent the smallest solid particles from falling down through the apparatus while facilitating a uniform inflow of solvent. A preferred fine mesh screen for processing dental dust is formed from polyester cloth having about a $225\mu$ pore size. Fine mesh screen 11 is sealed in position by an "O" ring 14, which surrounds downwardly depending edges of the screen. It can thus be relatively easily removed, if it deteriorates or becomes clogged, and can be cleaned and/or replaced by first removing the flexible O-ring.

Figure 7:
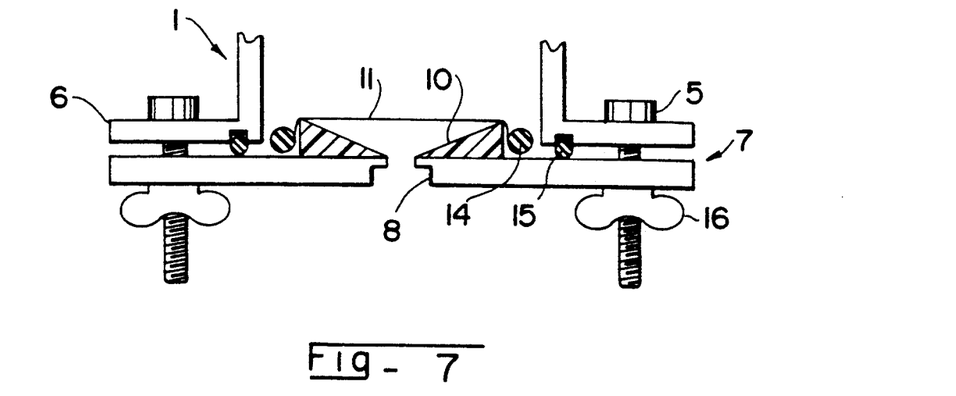
FIG. 7 is a cutaway longitudinal sectional view of the column components of FIGS. 4 and 5 in assembled form.

FIG. 7 is a sectional view of a preferred embodiment of the bottom member 7, and the lower end of column 1, in assembled form. Connecting bolts 5 pass through bolt holes 9. Wing nuts 16 are torqued onto the connecting bolts to enable "O" ring 15 to provide a seal between the top and bottom components.

Figure 8:
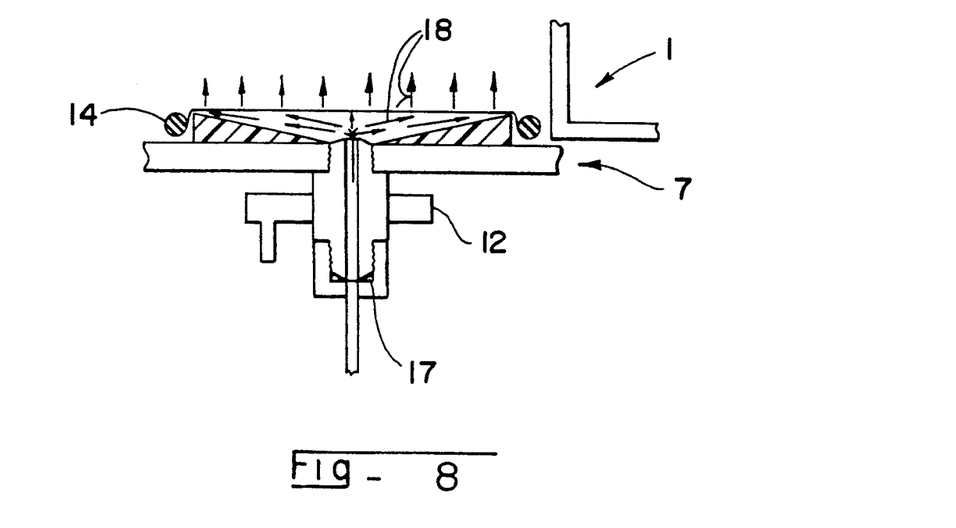
FIG. 8 is another longitudinal sectional view of the processing column of FIGS. 4 and 5 which depicts uniform flow.

The center portion of the bottom component 7 is tapered, as shown by the sectional view in FIG. 8, to effect a more uniform flow of solvent 18 through the solid material located within the column. FIG. 8 also shows an "O" ring 17 which provides a sealed connection between the inlet valve mechanism and the inlet tubing.

FIG. 9 illustrates an assembled column, as used in the system of FIG. 1, which has been loaded with bone particles 20. Top filter 19 prevents the outflow of particles and is preferably constructed of glass wool wrapped in cheesecloth. However, any screening material which is resistant to the solvents used in processing and inert to the reactions involved in the column, with a porosity smaller than the smallest particles in the column yet large enough to provide free outflow of solvent, may be used.

It is important that the bone particles occupy 80 to 90% of the column volume so that an optimum spacing between the particles and solvent flow therebetween is maintained. When a "normal" quantity of bone matrix (i.e., 300–400 gm) is to be processed, the column of FIGS. 4–8 is configured so that the sample occupies 80 to 90% of the column volume. As stated earlier, the column height of the preferred embodiment can be altered when the volume of bone to be processed is known prior to use. However, when a bone sample volume is not known in sufficient time to calculate and construct a column with a desirable height, and, therefore, when a column of proper dimensions cannot be predesigned, a plunger 21 may be positioned at the top of the column and slid into the column 1, as shown in FIG. 10 to reduce the effective volume of the column so that the bone particles occupy 80 to 90% of the effective volume of the column. The plunger 21 has an annular post which runs centrally through its length to allow solution to flow through to the outlet of the column.

Figure 11:
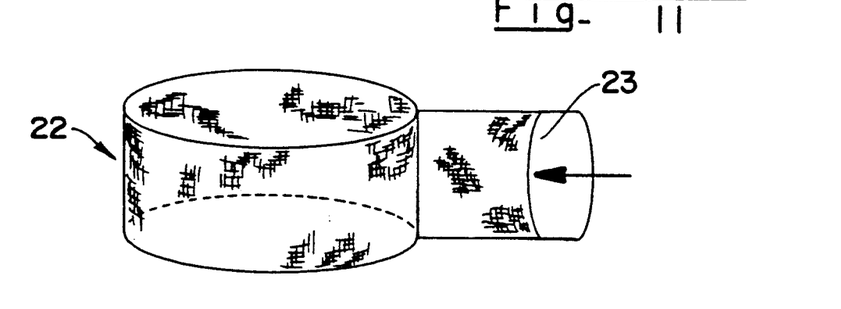
FIG. 11 is a plan view of a fine mesh bag which is used for processing, e.g., dental bone.
Figure 12:
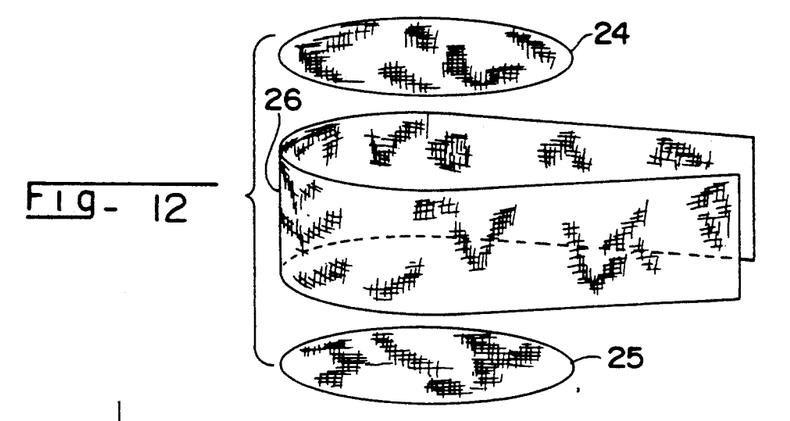
FIG. 12 is an exploded plan view of the fine mesh bag of FIG. 11.

FIG. 11 shows a fine mesh bag 22 which is preferably used as a container for the processing of dental bone or other bone. The fine mesh bag facilitates retention of the ground bone particles during processing. The fine mesh bag is preferably formed of polyester cloth which is resistant to absolute ethanol and up to 1.0N hydrochloric acid. The bag is formed of three panels as shown in FIG. 12. Circular discs 24 and 25 each have a diameter that is equal to the outside diameter of top component 1. Narrow strip 26 has a width which is approximately ¼" less than the height of column 1. The bag has a porosity of around 225μ and is thus of a small enough porosity to retain the smallest bone particles in the dental dust, which have a size of about 250μ, yet has a large enough porosity to permit formed gas (i.e., $CO_2$) to escape.

Figure 13:
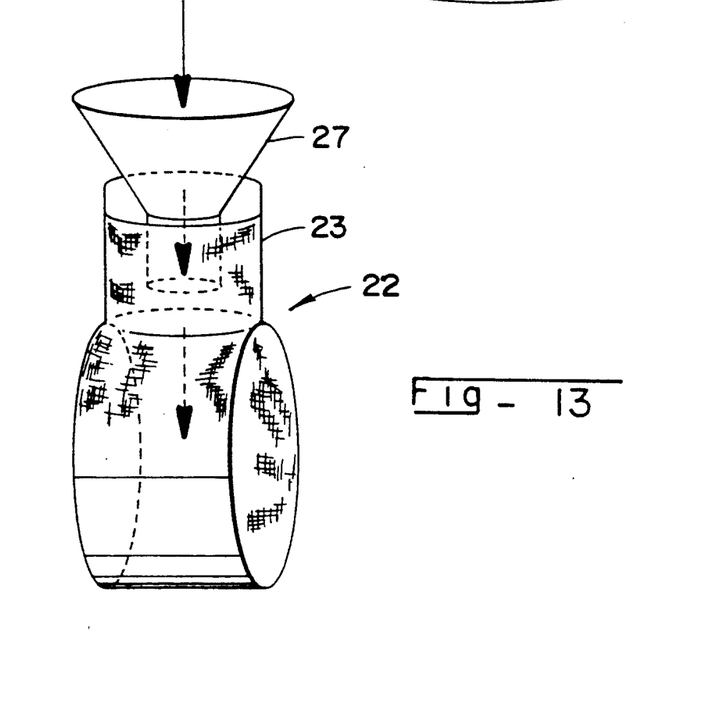
FIG. 13 is a plan view which indicates the loading of a fine mesh bag with the aid of a powder funnel.
Figure 14:
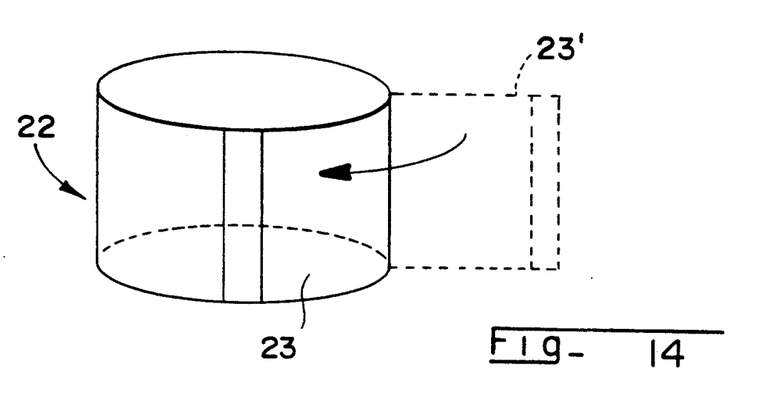
FIG. 14 is a plan view of a fine mesh bag with its filling spout in the closed position.

Loading of the fine mesh bag 22 is facilitated by a commercially available powder funnel 27 as shown in FIG. 13. Bone particles are loaded through bag filling spout 23. FIG. 14 shows the fine mesh bag fully loaded with bone particles and ready for insertion into the column, with the filling spout 23 having been folded around the outside of the bag. No closure devices are required to close the filling spout, since the snug fit of the filled bag against the inner walls of the column prevents the spout from opening. The filling spout is shown in the open position by phantom lines 23'.

The fine mesh bag at this stage may be placed into column 1, with bottom component 7 then being attached and bolted into place.

Further advantages obtained through the use of the fine mesh bag during processing are: easy addition and removal of the bag from the column; facilitation of a uniform flow of solvent through the bone particles in the bag; expansion and movement of the mass of bone particles in the bag as $CO_2$ gas is formed. The formation of $CO_2$ gas during demineralization effects a "stirring" of the confined bone particles which results in a more uniform demineralization of the particles. If the bone matrix initially takes up greater than 80-90% of the column volume, there is a danger of compaction of the bone particles when $CO_2$ gas begins to form, thereby restricting demineralization. The fine mesh bag further permits expansion of the bone mass since the bag material is deformable and resilient. The bone particles deform the bag upon expansion and when the bag resiliently returns to its original configuration, a stirring effect occurs. It is important that the outside diameter of the fine mesh bag fits easily and snugly into the inside diameter of the top component of the column device. A snug fit restricts the flow of solvent around the bag, thereby forcing the solvent flow through the bag so that a uniform flow of solvent interfaces with the bone particles therein, and also maintains the spout in a closed position.

Figure 15:
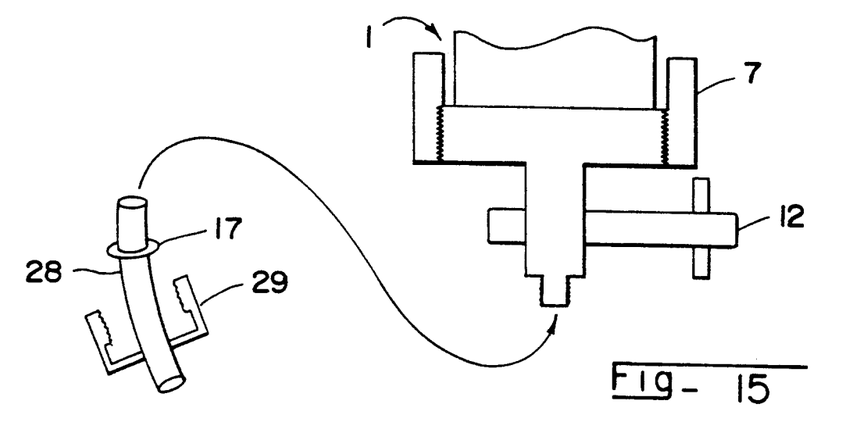
FIG. 15 shows the connection of an inlet tubing with the inlet port of a processing column.

FIG. 15 is a sectional view showing the connection of inlet tubing 28 to inlet valve means 12. Threaded cap 29 engages the threads on inlet valve means 12 to enable "O" ring 17 to sterilely seal the connection.

Figure 16:
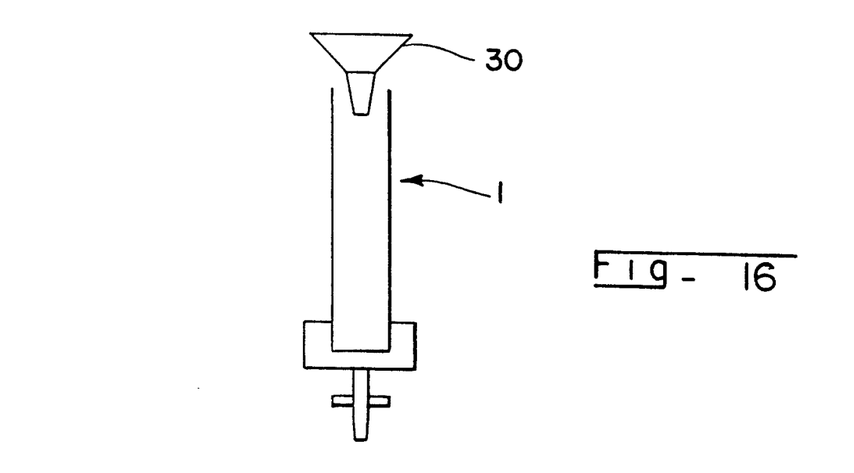
FIG. 16 shows the filling of an alternate embodiment of a column of FIG. 1, which does not require a fine mesh bag.

FIG. 16 shows an alternate method of loading a column which is more often used for bone particles of larger dimension than dental bone. Funnel 30 facilitates direct loading of bone particles into column 1, without the use of a fine mesh bag positioned within the column. Columns may also be loaded directly with, e.g., cortical strips of bone for demineralization.

Once the column is filled and the bottom component is connected with the column, the column is assembled into the apparatus as shown in FIG. 1.

Advantageously, once the bone sample has been loaded into column 1 and connected in line with the apparatus of the present invention, it is sterilely sealed and there is no requirement to ever break the sterile seal until such time as the sample is to be freeze-dried and dispensed. More specifically, the column is connected to the inflow and outflow lines of the apparatus and inflow and respective outflow valves 12 and 2 are opened to permit solutions to be selectively flowed through column 1. Both inflow and eluent (outflow) sides of the column ensure sterility of the column with the various in-line filters. The flow control detector 39 and controller 38, as described earlier, permit the switching of different solution flows through the column without ever having to disconnect and reconnect any tubing The advantage of this is that the entire system remains sealed and sterile.

Upon completion of flow of all processing solutions through columns 1, inflow and outflow valves 12 and 2 are closed to sterilely seal the inner contents of each column from the rest of the apparatus. Each column can then be removed from its clamp supports 33 and stored for future use. Optionally, adapters (which can have, e.g., flat support surfaces) may be threaded onto the inflow end of inflow valve 12 and the outflow end of outflow valve 2, to enable secure storage of columns on a vertical (or other) orientation. Thus, there is no requirement to expose the treated sample to a non-sterile environment and the sample can be frozen in its sterile condition within column 1.

Further details of the process of the invention are presented in the examples that follow:

EXAMPLE 1

Demineralization of Dental Bone

Properly sized ground bone (250μ to 700μ) is placed into the fine mesh bag, as described above, and placed into the column. The column is closed and placed into a clamping device such that it is level.

Utilizing a peristaltic pump, solvents are pumped into the column through the inlet port and outwardly from the outlet port. The valves placed at each of these ports are designed to permit sealing of the system prior to and after processing to ensure that the bone materials will remain sterile. Bone particle processing proceeds as described:

1) Ethanol (95% Ethanol, 5% water [deionized]; sterile) is pumped rapidly into the column until full. At this point, the bone particles may be left to "soak" in the ethanol for a prescribed time interval, with changes in ethanolic solution (i.e., adding fresh solution to replace the original volume of ethanol), until ethanol extractable lipids are extracted. Alternatively, ethanolic solution may be continuously pumped through the bone, at a flow rate of approximately one (1) ml per minute. At this flow rate, approximately 84 mg of ethanol soluble lipid should be extractable per 10 gms of bone matrix. This value will vary from donor tissue to donor tissue. The volume of ethanol required should approximate 90.0±5.49 mls/10 gms of bone, although this value may also vary with donor tissues. Elution of ethanol soluble lipids may be monitored by measuring absorbance of eluent solution at 210 nm. As an alternative, less sensitive assay eluent may be dropped dropwise into deionized water in a small test tube. If lipids are present in the eluent ethanol, a cloudy precipitate will appear in the upper part of the aqueous volume as the dissolved lipids come out of solution Sterile deionized water is pumped into the column to displace the ethanolic solution. Alternatively, the ethanolic solution may be replaced with acid solution such that demineralization commences immediately. Problems to watch for at this point include, but are not limited to, the potential for formation of lipid micelles if ethanol soluble lipids are still present to an appreciable extent in the ethanolic solution. Such lipid micelles may absorb onto the bone particles. The effects of such absorption on activity of bone product (i.e., osteoinduction) are unknown at present. Demineralization of bone particles is accomplished by pumping 0.5N HCl through the bone particles at a flow rate of approximately one (1) ml per minute. Data developed by the inventor indicates that minerals (assayed as $CaCl_2$) should be extracted at approximately 0.042 gms/ml acid and that extraction should be "complete" (i.e. less than 5% by wt. calcium) with use of approximately 160 mls acid per 10 gms of bone. The values are projections based on the use of larger bone particles in a less favorable column geometry and thus, although values will vary from donor tissue to donor tissue, it is expected that with the smaller bone particles in dental bone, minerals will be extracted more efficiently utilizing less volume of acid. "Completion" of demineralization may be monitored utilizing a calcium-specific electrode, measuring calcium ion concentrations in the eluent, or by monitoring pH of the eluent. A potential problem during processing is the formation of gas bubbles as the acid contacts the bone particles. It is suggested that this gas is $CO_2$ evolving as the acid reacts with calcium carbonate in the bone. If acid is pumped too rapidly, gas formation can be excessive and should the outlet port become clogged, pressure can build up in the device and cause leaks around the "O" ring between the column and its member. The formation of gas can be beneficial, in that it "stirs" the bone particles as it rises upwards through the bone particles, escaping through the outlet port.

EXAMPLE 2

Demineralization of Cortical Strips

| Column Information: | |
|---|---|
| Height | 30 cm |
| Diameter | 1.4 cm |
| Volume | 52 ml |
| Weight of bone | 14.532 g |
| Height of bone at commencement of experiment | 13.5 cm |
| Height of Cheesecloth at commencement of experiment | 8 cm |

A column of bone particles were filled with absolute ethanol and allowed to soak for 16 hours. A volume of 143.8 ml. of ethanol was then flowed through the column at a flow rate of 1.2 ml./minute. The delipidization phase was then terminated and a total volume of 200 ml., of sterile distilled water was flowed through the column at a rate of 6.8 ml./minute.

The demineralization phase began by running 228 ml. of 0.5N HCl through the column at a rate of 0.95 ml/minute. The eluent pH at the end of this run was 0.26. Another volume of 200 ml of sterile distilled water was then run through the column at a rate of 0.19 ml/minute.

Five pieces of bone, which were still somewhat rigid, were removed from the column and lyophilized. The weight of the bone before lyophilization was 7.336 g. The weight of the bone after lyophilization was 5.793 g.

The remaining pieces of bone in the column received 1800 ml more of 0.5N HCl at a flow rate of 0.43 ml/minute. The eluent pH at the end of this run was 0.28. A volume of 200 ml of sterile distilled water was then run through the column at a flow rate of 6.8 ml/minute.

The remaining pieces of bone were removed. These pieces, being pliable, were lyophilized. The weight before lyophilization was 5.266 g, and after lyophilization the weight of these bone samples was 1.922 g.

EXAMPLE 3

Demineralization of Ground Cortico/Cancellous Bone

Cortico/Cancelleous bone fragments were ground to a heterogeneous size. Approximately 90 gms of bone matrix was packed into a column (2.5 cm I.D. by 60 cm in height). The height of the bone matrix was approximately 40 cm. A small "ball" of glass wool wrapped in cheese cloth was placed on top of the bone matrix and a column plunger was placed into the column and run down to slightly compress the ball of glass wool/cheesecloth. The column was sealed and absolute ethanol pumped through the matrix at a flow rate of 3.7 ml/minute. Lipid in the eluent was monitored by dropping ethanolic eluent into water and observing for a cloudy precipitate. In this instance a more sensitive form of this assay was used, collecting 6.8 ml fractions and adding 6.8 ml of water, watching for a cloudy precipitate as an indication of the presence of lipid in the eluent. Complete removal of ethanolic extractable lipids required 2,477 ml (and included an overnight "soak" of the bone matrix in ethanol). A total of 390 mls of distilled water was used, at a pump rate of 3.7 mls/minute, to remove the ethanol (390 mls represents the approximate volume of the column, i.e. one column volume of water) was used to elute the ethanol. With a flow rate of 3.7 ml/minute, this "washing" required approximately 100 minutes (1 hr., 40 min). Then, the solvent is switched to 0.5N HCl, at a flow rate of 3.7 ml/minute, and the acid is pumped through the bone to affect demineralization. By monitoring pH, demineralization was essentially completed by 300 ml (Note: calcium ion concentration in the eluent acid always paralleled and followed the pH profile. At a flow rate of 3.7 ml/minute, demineralization thus required approximately 82 minutes. Buffer was not run over the bone, as it was preferred to run distilled water (1,580 ml). The pH was returned to approximately 6.2. The bone matrix was then freeze-dried for 2 days and weighed. The weight of the freeze-dried bone was 40.33 gms.

The experimental protocol for the demineralization process of Example 3 is as follows:

1) Grind bone matrix as per standard protocol for producing cortico/cancellous bone matrix. Expect bone matrix to approximate 90 to 100 gms as a "donor lot". This bone mass may be exceeded by 10 to 20% and still utilize the column indicated below. All procedures were conducted at room temperature.

2) Screw the bottom plate onto a 60 cm×2.5 cm (I.D.) glass column and pour the bone matrix into the column. Shake gently to "compact" the bone matrix. Do not compact tightly.

3) Place a small ball of glass-wool wrapped in cheese cloth on top of the bone matrix and insert the column plunger until it slightly compacts the ball. Do not compress the bone matrix. Seal the column endplates and open valves after attaching tubing.

4) Place the column, with bone matrix, into the column holding device, bottom plate down and attach the tubing to the solvent distribution apparatus. Place outlet tubing into waste container. All solvents will be run bottom to top of bone matrix.

5) Run 95% ethanol into the column, until it begins to flow from the outlet line (approximately 100 to 200 mls, depending on bone matrix and corresponds to a "column volume" as used below). Let stand at room temperature for 30 minutes.

6) Run an additional volume of 95% ethanol into the column and let stand for 30 minutes. Repeat this to a minimum of one additional time (3 to 4 times total), i.e. a total volume of ethanol of 500 ml for every 100 gms of bone matrix and a total extraction time of approximately 2 hrs. Note: To monitor for lipid extraction, add approximately 5 ml of ethanol eluent into a test tube and add an equal volume of water. A cloudy precipitate indicates that lipids are still present in the eluent ethanol. Lipids will most probably be present.

7) Run 0.5N HCl onto the column at a flow rate of approximately 4 ml/minute and monitor the pH of the eluent, beginning after approximately 200 ml of acid. When pH has fallen to approximately pH 1.0 to 2.0, run acid for an additional 100 ml of acid.

8) Run 3 column volumes (a column volume equals that volume of ethanol that is required to fill the column initially) of distilled water over the bone matrix. This flow rate may be that which is maximally possible based on the tubing diameter utilized.

9) Run 3 column volumes of 0.02M potassium phosphate buffer (pH 7.4) onto the column, at maximal flow rate. Check the pH of eluent solution near the end of the buffer run. It should be approximately 7.0 to 7.4).

10) Run 6 column volumes of distilled/deionized water onto the column, maximum flow rate possible. If you wish to check pH near the end of this run, add 2 ml of 1M KCl/100 ml of solution and check pH using a calibrated pH meter. It should be approximately pH 6.

11) Close column valves (both ends) and remove column from the column holding device and invert the column. Disconnect tubing from solution distributing device and open valve on column bottom and then valve on column top (this means original top and bottom, not present top and bottom) and allow solution to drain from the column into a waste container. Care should be taken at this point not to introduce microbial contamination, and optionally an in-line air filter may be added to the "air inlet" line. To effect this draining, the column may be reclamped in the column holding device "up side down" and left to drain.

12) Remove bone matrix from column after removing end plates and/or plunger. Dry.

Thus, a preferred process includes the loading of bone particles or pieces into at least one column, either directly or by first loading the bone into a fine mesh bag and then placing the fine mesh bag into the column. Each bottom plate is then sealed and secured to each column, and each column(s) is secured in a vertical position with the column clamps.

Inlet and outlet tubing is connected to the input and output valves respectively. The flow of solutions is then commenced through the column(s). Ethanol is generally the first solution that is passed through the column to delipidize the bone. Sterile distilled and/or deionized water may optionally be run through the column after the ethanol run, to wash the bone, or an acidic solution, preferably HCl may be run immediately following the ethanol run to demineralize the bone. Optional solutions may be passed through the column(s) after the demineralization run is complete, to include, sterile distilled and/or deionized water; solutions of vitamins, antibacterial agents, antifungal agents, bone morphogenetic protein and the like.

Solution flow begins at the solution reservoirs and proceeds through optional flow meters, through in-line filters, then through a flow control/switching mechanism which may be manually or computer controlled. The flow control/switching mechanism may be pneumatically driven or driven by electric solenoid. Flow then proceeds to at least one pumping mechanism which provides the driving force for the flow throughout the entire apparatus. The pumping mechanism pumps the solution through an in-line filter through each inlet port and into each column. The solution interfaces the solid bone particles/pieces as it flows through the column(s), exits the outlet port(s), passes through optional detecting devices, optional flow rate monitor and into a waste receptacle.

The flow rate monitors and detecting mechanisms provide feedback to the computer controller. The computer controller uses the feedback to maintain desired rates of flow of solutions, and to determine when each particular phase of processing is complete Upon completion of a phase of processing, the computer signals the flow control/switching mechanism to shut off flow from the current solution reservoir and to open flow from the next successive solution reservoir. The computer controller is programmed to continually monitor solution flow and to switch solution sources at the proper times until processing is complete.

Upon completion of the delipidization/demineralization process, including any washing steps or other treatments mentioned earlier, the switching mechanism is directed to shut off all flow of solutions through the column(s). The inlet and outlet valves are then closed on the columns, and after draining the column(s) of any remnant solution, the bone samples may be directly stored in the column(s) in a sterile condition.

Although the invention has been described with reference to particular means, materials and embodiments, it is to be understood that the invention is not limited to the particulars disclosed and extends to all equivalents within the scope of the claims.

What is claimed is:

1. A process for extracting undesirable constituents of bone comprising:
   loading said bone into at least one column, each said column comprising an inlet and an outlet means;
   flowing a first solution through each said column;
   detecting a characteristic of a first solute which is present in said solution as said first solution exits each said column;
   terminating flow of said first solution once a desired characteristic of said first solute is detected.

2. The process of claim 1, further comprising:
   flowing a second solution through each said column, upon said termination of flow of said first solution;
   detecting a characteristic of a second solute which is present in said second solution as said second solution exits each said column; and terminating flow of said second solution once a desired characteristic of said second solute is detected.

3. The process of claim 2, further comprising:
flowing a third solution through each said column and;
detecting a characteristic of a third solute which is present in said third solution as said third solution exits each said column.

4. The process of claim 3, wherein said third solution flow is continuously monitored until said termination of flow of said third solution.

5. The process of claim 3, wherein detecting said third solute concentration comprises detecting the pH of said third solution.

6. The process of claim 3, wherein said third solute comprises calcium ions and detecting said third solute concentration comprises detecting the calcium ion concentration of said third solution.

7. The process of claim 3, wherein said third solute comprises calcium and detecting said third solute concentration comprises detecting conductivity with a calcium specific electrode.

8. The process of claim 2, wherein said second solution flow is continuously monitored until said termination of flow of said second solution.

9. The process of claim 2, wherein said first solution comprises a lipophilic solvent and said second solution comprises water.

10. The process of claim 2, wherein said first solution comprises a lipophilic solvent and said second solution comprises acid.

11. The process of claim 2, wherein detecting said second solute concentration comprises detecting the absorbance of said second solute.

12. The process of claim 2, wherein detecting said second solute concentration comprises dripping a sample of said second solution into deionized water to determine whether a precipitate forms.

13. The process of claim 2, wherein detecting said second solute concentration comprises detecting the pH of said second solution.

14. The process of claim 2, wherein said second solute comprises calcium ions and detecting said second solute concentration comprises detecting the calcium ion concentration of said second solution.

15. The process of claim 2, wherein said second solute comprises calcium ions and detecting said second solute concentration comprises detecting conductivity using a calcium specific electrode.

16. The process of claim 1, wherein said first solution flow is continuously monitored until said termination of flow of said first solution.

17. The process of claim 1, wherein detecting said first solute concentration comprises detecting the absorbance of said first solute.

18. The process of claim 1, wherein detecting said first solute concentration comprises dripping a sample of said first solution into deionized water to determine whether a precipitate forms.

19. The process of claim 1, wherein said bone comprises particulate bone or strips of cortical bone.

20. The process of claim 1, wherein said bone is loaded into at least two columns.

21. The process of claim 1, wherein said bone is loaded into a plurality of columns.

22. The process of claim 1 wherein each said column is attached to a demineralization apparatus during processing and removed from said apparatus after processing to enable said bone to be stored within each said column.

23. The process of claim 1, wherein said bone is stored in each said column after processing.

24. The process of claim 1, wherein flow control is accomplished pneumatically.

25. The process of claim 24, wherein said pneumatic control is further controlled by computer.

26. The process of claim 1, wherein flow control is accomplished electrically by actuating at least one solenoid controlled valve.

27. The process of claim 26, wherein said electrical control is further controlled by computer.

28. The process of claim 1, wherein flow is computer controlled.

* * * * *